United States Patent [19]

Savaides et al.

[11] Patent Number: 5,637,297
[45] Date of Patent: Jun. 10, 1997

[54] REDUCING AGENTS FOR PERMANENT WAVING OF HAIR

[75] Inventors: Andrew Savaides, Norwalk, Conn.; Edward Borish, Mahwah, N.J.; Thomas M. Schultz, Ridgefield, Conn.; Sanae Kubo, Darien, Conn.; Adalberto Fleitas, Norwalk, Conn.

[73] Assignee: Shiseido Co., Ltd., Tokyo, Japan

[21] Appl. No.: 352,386

[22] Filed: Dec. 8, 1994

[51] Int. Cl.$^6$ .................. A61K 7/06; A61K 7/09
[52] U.S. Cl. .................. 424/70.51; 424/70.5; 424/70.2; 132/204; 132/205; 132/206
[58] Field of Search .................. 424/70.2, 70.5, 424/70.51; 132/204, 205, 206

[56] References Cited

U.S. PATENT DOCUMENTS

| | | | |
|---|---|---|---|
| 4,153,681 | 5/1979 | Shiba | 424/70.51 |
| 4,218,435 | 8/1980 | Shiba | 424/70.51 |
| 5,332,570 | 7/1994 | Bergstrom et al. | 424/70.51 |

FOREIGN PATENT DOCUMENTS

90/03780  4/1990  WIPO.

OTHER PUBLICATIONS

Zviak, The Science of Hair Care, pp. 189–203 1986.

Primary Examiner—Sally Gardner-Lane
Attorney, Agent, or Firm—Melvin I. Stoltz, Esq.

[57] ABSTRACT

An improved, highly effective permanent waving lotion is attained by employing a reducing agent which consists of a lower alkyl ester of cysteine in combination with a thiol compound selected from the group consisting of ammonium salts and glyceryl esters of thioglycolic acid, thiolactic acid and thiopropionic acid. By employing the reducing agent of this invention, the pH level at which the permanent wave is performed can be substantially reduced, thereby improving comfort and reducing adverse reactions. The reducing agent of this invention is employed either as an aqueous solution of the two components or in association with desired additives for imparting additional benefits to the permanently waved hair. Preferably, the reducing agents of the present invention are employed in a permanent waving lotion having a pH ranging between about 5.0 and 9.5.

15 Claims, No Drawings

REDUCING AGENTS FOR PERMANENT WAVING OF HAIR

TECHNICAL FIELD

This invention relates to the art of permanently waving hair, and more particularly, to novel additives or compositions for use in combination with conventional reducing agents to provide substantially increased, long-lasting, durable permanently waved hair while also substantially reducing the pH level employed by the conventional reducing agents.

BACKGROUND ART

The permanent waving of hair is a well established and well developed art in which substantial attention has been directed to improve the present level of technology. Although substantial changes have occurred throughout the last decades, various problems continue to plague the industry in spite of numerous attempts to reduce or eliminate these problems.

In order to best understand the present state of the art and the problems existing therein, it is important to reiterate that hair fibers are composed of a unique protein called "keratin" which is distinguished by the fact that it contains a very significant amount of an amino acid (cystine) which contains the element sulfur in addition to the elements nitrogen, oxygen, carbon and hydrogen. In the natural synthesis of hair, the element sulfur covalently links intra or inter polypeptide chains (K) through two sulfur atoms (S—S) to give keratin protein (K-S-S-K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for the cold permanent waving of hair. Typically, these prior art systems treat the hair with reducing agents which break the disulfide (cystine) linkage in the hair, while the hair is wound around a curling rod.

In general, permanent hair waving is usually carried out by subjecting the hair to reagents containing a free—SH group or thiol. These materials are also called mercaptans. In this treatment, the hair usually is either wrapped on the rods with water or the lotion containing the thiol, and then saturated with thiol lotion. The thiol waving agent acts to break the disulfide bonds within the hair fiber forming thiol groups in the hair protein and disulfide bonds between two thiol waving agent molecules. The chemistry involved in the reaction of the mercaptan with the cystine disulfide bonds in the hair fiber is illustrated by the following chemical equations (i), (ii) and (iii):

(i) KSSK+RSH⇌KSH+RSSK (ii) RSSK+RSH⇌KSH+RSSR (iii) KSSK+2RSH⇌2KSH+RSSR

When a sufficient number of hair disulfide bonds have been broken, the hair is realigned to pair previously unpaired hair protein thiol groups opposite each other. At this point, the hair is rinsed, removing the unreacted thiol waving agent and any water soluble disulfide reaction product formed from it. Then, the hair is saturated with an oxidizing agent, or neutralizer, such as hydrogen peroxide or bromate salt, to reform disulfide bonds between the newly paired hair protein thiols, thereby giving the hair a new configuration or wave, or adding curl to the hair. By rebonding the sites of the reduced keratin in their new curled configuration, a permanent set which is impervious to water is established.

Much of the rebonding of the reduced sites is accomplished by the action of the chemical oxidizing agent, which is typically hydrogen peroxide, and can be illustrated by the following chemical reaction:

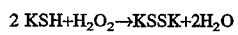

$$2\ KSH + H_2O_2 \rightarrow KSSK + 2H_2O$$

The most commonly used reducing agents employed in the permanent deformation of hair keratin are salts and esters of thioglycolic acid. Other less commonly used reducing agents include cysteine, cysteamine, thiolactic acid and their derivatives. These reducing agents are very effective in the reduction of disulfide bonds and under certain conditions can reduce more than 50% of the keratin cystine bonds.

Although effective in providing excellent reducing capabilities, the above mercaptans and their corresponding derivatives possess problems that are difficult to control. One of the disadvantages is the fact that permanent waving must typically be conducted at elevated pH levels. However, since the skin surface of humans is usually at a weak acidic level, the use of products at an elevated pH causes discomfort, irritation, and/or adverse reactions. Although low pH levels would be desirable, the permanent wave results produced at lower pH levels are not satisfactory. Other disadvantages of prior art reducing agents are the irreversible fiber alteration as made evident by increased fiber porosity and decreased tensile properties.

Much efforts have been expended in attempts to minimize these attributes. These include pretreatments, barriers which decrease the rate of diffusion, reduction of the mercaptan concentration and/or the pH of the reducing agents, and duration of reduction time. Many of these pretreatments yield other undesirable characteristics such as oily, greasy, and dirty feeling of the hair fiber.

Furthermore, in the art of permanent waving, there is much trial and error, with the hair being over-processed, in some instances. The characteristics of over-processing are raspy feel to the hair or a loss of the natural underlying color. Structural evaluation of the hair fiber by instrumentation usually reveals that the structural integrity of the hair is lessened, which is evidenced by either an increase in the amount of cysteine and cysteic acid or a lessening of the cystine content relative to the hair not so processed.

Some detrimental effect to hair fiber is unavoidable, as the process of permanent waving involves controlled bond scission of the disulfide linkages within the keratin proteins. Recovery of these disulfides is the determining factor for the tightness of the curls and overall tensile strength. Typically, in order to reshape hair fibers into a lasting configuration, 20% to 50% of available disulfide bonds must be cleaved and reformed into the new configuration. If insufficient disulfide bonds are broken, the hair fiber will rapidly regain natural configuration.

In spite of the substantial effort that has occurred in the development of various permanent waving composition of this general nature, there has been a general inability to improve the holding power or curl configuration retention of "cold permanent waving" formulations. The typical problem encountered with the use of mercaptan reducing agents for the permanent waving of hair is that the permanency of the curl will not last until it is cut off. Instead, the curl relaxes slowly from the normal wear and tear of every day hair care. In this normal grooming process of shampooing, combing, drying and brushing the hair, the fibers are constantly being put under tension and exposed to forces that oppose the new disulfide and hydrogen bonds that were created in the new curl configuration.

In addition to longer curl retention, the industry has also sought to increase the luster, sheen, gloss and manageability of the hair, as well as provide a permanently waved head of hair which is soft, supple, and possesses a natural feel. However, these goals have not been fully attained.

Furthermore, permanent change in hair keratin coupled with operator error, provides inevitable damage to the hair fibers. This damage is measured by evaluating the tensile strength of hair keratin fibers caused by these chemical treatments. Therefore, it would be advantageous to provide treatments that would produce results of a permanent nature and minimum damage to hair keratin.

Since physical and chemical changes in the keratin structure of hair fibers are observed during the deformation and relaxation of hair, researchers have tried to minimize the rate of hair relaxation caused by natural forces and water, utilizing treatments of naturally occurring or synthetic polymers. Some surface polymer treatments have had temporary effect on promoting cohesion and decreasing or retarding the rate of water uptake by the hair fiber, while other treatments have attained temporary improvement of such physical characteristics as sheen, manageability and strength. However, these prior art conditioning agents merely provide a temporary benefit and are incapable of satisfying the long-felt need for substantially permanent hair condition improvement.

Therefore, it is a principal object of the present invention to provide a composition for permanently waving hair fibers which is capable of imparting to the head of hair a durable, long-lasting permanent hair set retention, while substantially reducing the pH level typically required for the waving process.

Another object of the present invention is to provide a permanent wave composition having the characteristic features described above which is capable of conditioning the hair fibers and improving physical properties of the treated hair such as shine, luster, softness, manageability, hair body, and thickness.

Another object of the present invention is to provide a permanent wave composition having the characteristic features described above which is capable of imparting a long-lasting permanent wave or setting property to the hair, while substantially reducing hair damage caused during the reduction and oxidation processes.

A further object of the present invention is to provide a permanent wave composition having the characteristic features described above which is capable of improving the elastic and tensile properties of the hair fibers.

Other and more specific objects will in part be obvious and will in part appear hereinafter.

DETAILED DESCRIPTION

By employing the present invention, the prior art limitations and difficulties have been overcome and a long lasting, permanently waved head of hair is attained using a new permanent waving composition which is capable of being employed at pH levels substantially lower than pH levels previously required. In addition, the permanent waving lotion composition of the present invention provides a greater control over the curl formation process while also enhancing the physical properties of the hair fibers, such as feel, shine, luster, softness, and manageability.

In accordance with the present invention, desirable, and previously unattainable, enhanced characteristics and operating conditions are realized by employing a suitable concentration of a lower alkyl ester of cysteine in combination with an aqueous solution of one thiol compound selected from the group consisting of ammonium salts and glyceryl esters of thioglycolic acid, thiolactic acid and thiopropionic acid. In order to provide the enhanced beneficial result, the concentration of the lower alkyl ester of cysteine should range between about 0.01% and 10% of the final composition of the permanent waving lotion.

It is well known to one of ordinary skill in the art that a thiol compound selected from the group consisting of ammonium salts and glyceryl esters of thioglycolic acids and thiolactic acids can be employed independently as a permanent waving lotion. In addition, it is taught in U.S. Pat. No. 4,153,681 that the lower alkyl ester of cysteine or a salt thereof may be employed as the sole reducing agent in a permanent waving lotion. More recently, co-pending patent application, bearing Ser. No. 08/305,574 and a filing date of Sep. 14, 1994, which is owned by the Assignee of this application, discloses that glyceryl esters of thiopropionic acids can be employed either individually or in combination as the sole reducing agent in a permanent waving lotion.

Although these references specifically teach the use of these chemicals as reducing agents, the prior art is completely devoid of any teaching which suggests the combination of a lower alkyl ester of cysteine with one thiol compound selected from the group consisting of ammonium salts and glyceryl esters of thioglycolic acid, thiolactic acid and thiopropionic acid. Preferably, the lower alkyl ester of cysteine comprises one selected from the group consisting of methyl-cysteine, ethyl-cysteine, and propyl-cysteine. It is this specific, unique combination of chemicals which provides the substantially enhanced and improved permanent waving lotion of this invention and the resulting benefits realized thereby.

As discussed above, one principal benefit attained with the combination of a lower alkyl ester of cysteine with the thiol compounds defined above is a substantial reduction in the pH level at which the permanent waving process is conducted. In general, it has been found that the pH level is reduced by between about 1 and 3.5 pH units by incorporating the lower alkyl ester of cysteine in combination with the thiol compound, with the lower alkyl ester of cysteine ranging between about 0.01% and 10% by weight based upon the entire weight of the permanent waving lotion.

It has also been found that the most advantageous results are attained with the lower alkyl ester of cysteine comprising ethyl-cysteine and having a range of between about 0.01% and 5% by weight based upon the entire weight of the permanent waving lotion. With this quantity of ethyl-cysteine in combination with the desired thiol compound, a substantial pH reduction is attained along with greater control of the curl formation and a better feel to the resulting permanently waved hair.

In addition to the combination of a thiol compound and a lower alkyl ester of cysteine, as detailed above, the permanent waving lotion may also incorporate additional additives commonly employed. These additives impart additional benefits to the resulting permanently waved hair and include conditioning agents, fragrances, surfactants, and alkalizing agents, used to maintain the desired pH level. In the preferred compositions, the alkalizing agent is selected from the group consisting of ammonia, ammonium hydroxide, monoethanolamine, guanidine, diethanolamine, triethanolamine, ammonium carbonate and bicarbonate.

In preparing the permanent waving lotion in accordance with the present invention, an aqueous solution containing any desired surfactants, conditioning agents, and fragrances is separately prepared. Then, immediately prior to the application of the waving lotion to the hair, the conditioning agents are intermixed with an aqueous solution of the thiol compound combined with the lower alkyl ester of cysteine. Finally, the pH of the resulting composition is adjusted using the desired alkaline agent to produce a pH level ranging between about 5.0 and 9.5. The resulting permanent waving and reducing lotion is then ready for immediate use on any desired head of hair.

In Table I, an overall general composition of a permanent wave reducing lotion made in accordance with the present invention is provided. By referring to this formulation, the various desired ingredients and quantity of each ingredient is detailed on a percent by weight basis, based upon the entire weight of the entire composition.

TABLE I

PERMANENT WAVE REDUCING LOTION COMPOSITION

| INGREDIENT | WEIGHT PERCENT RANGE |
| --- | --- |
| Thiol Compound | 1 to 25% |
| Lower Alkyl Ester of Cysteine | 0.01 to 10% |
| Surfactants | 0.1 to 4% |
| Conditioner Agents | 0.1 to 6% |
| Alkalizing Agent | 0.1 to 10% |
| Fragrance | 0.5 to 3% |
| Water | q.s. to 100% |

In employing the present invention, a generally conventional application process is employed. In this regard, the permanent wave reducing lotion detailed above can be employed or, if desired, an aqueous solution of the thiol compound and lower alkyl ester of cysteine can be employed. Regardless of which composition is employed, the same generally conventional application process is used.

In this application process, the dual-component reducing agent or the permanent wave reducing lotion is applied directly to freshly shampooed and moistened hair, which has been previously rolled on rollers. The hair fibers are thoroughly wetted by the dual-component reducing agent or the permanent wave reducing lotion, which is then allowed to remain on the moistened hair for between about 10 and 60 minutes. Although this range has been found to be effective, the dual-component reducing agent or lotion is preferably allowed to remain on the hair for between about 5 and 30 minutes. If desired, the reaction may be accelerated by applying heat to the hair. However, it has been found that heat is usually not required.

Once the desired reaction time has been achieved, the hair is rinsed with water and blotted to remove excess moisture. Then, the hair is neutralized or oxidized with a solution which incorporates one or more agents selected from the group consisting of acidic hydrogen peroxide, alkaline bromate, and sodium chlorite. Preferably, the oxidizing solution is applied to the hair and allowed to remain on the hair for between about 2 and 10 minutes. However, alternate time ranges can be employed without departing from the scope of this invention. Finally, the hair tresses are rinsed with running water for two minutes, unwound from the rod, and allowed to dry.

By employing the present invention, a substantially improved and enhanced permanently waved head of hair is attained. Furthermore, the reduction process is conducted at a substantially reduced pH level, thereby increasing the comfort of the application process for the recipient. In addition, the present invention provides physical characteristics, such as gloss, combability, and softness to the resulting permanently waved hair, while also substantially increasing curl retention or hair set permanency. As a result, the present invention is capable of eliminating most of the prior art problems while providing a highly effective reducing lotion for permanently waving heads of hair in a more comfortable manner with substantially improved results.

The invention accordingly comprises the several steps and relation of one or more such steps with respect to each of the others and the composition possessing the features, properties and relation of components, all as exemplified herein with the scope of the invention being indicated in the claims.

BEST MODE FOR CARRYING OUT THE INVENTION

In order to substantiate the efficacy of creating a reducing agent consisting of a lower alkyl ester of cysteine in combination with one thiol compound selected from the group consisting of ammonium salts and glyceryl esters of thioglycolic acid, thiolactic acid, and thiopropionic acid, the following examples are presented. Preferably, the lower alkyl ester of cysteine comprises one selected from the group consisting of methyl-cysteine, ethyl-cysteine, and propyl-cysteine. In this disclosure, the efficacy of the present invention is clearly detailed, along with the ability of the composition of the present invention to permanently wave hair with substantially improved, long-lasting, physical enhancements and characteristics being realized thereby. However, it is to be understood that the following examples are intended as a teaching of the best mode for carrying out the present invention and are not intended to limit the breadth of this discovery.

As is evident from a review of the following examples, the present invention is centered upon the discovery that a suitable concentration of a lower alkyl ester of cysteine in combination with an aqueous solution of one thiol compound selected from the group consisting of ammonium salts and glyceryl esters of thioglycolic acid, thiolactic acid, and thiopropionic acid produces a reducing agent that provides substantially enhanced benefits. In particular, as clearly shown herein, the reducing agent of the present invention enables the permanent waving process to be conducted at a pH level substantially lower than previously attainable with prior art compositions, while also producing a resulting permanently waved head of hair having greater curl formation control and better feel.

In order to prove the efficacy of the present invention, numerous hair tresses were tested by being permanently waved using the compounds of the present invention as the reducing agent and comparing these results to hair tresses permanently waved with conventional reducing agents. In order to provide a standard by which the waving efficiency of the reducing agents can be objectively evaluated, the "Deficiency in Wave Tightness" (DIWT) was determined for each sample and compared.

In determining the Deficiency in Wave Tightness (DIWT), the Test Tube Test Curl (TTTC) procedure was used for each reducing agent at each pH level. In accordance with this procedure, twelve freshly shampooed, normal human hair fibers were knotted at the root end and cut to a length of 3.5 inches from the knot. The bundle was immersed in water and then wound around an aluminum mandrel having a diameter of 6.5 mm. Thereafter, the bundle and mandrel were immersed into 15 ml of the reducing solution (1.0N) at a constant temperature of about 37° C., and allowed to remain for 10 minutes. Once completed, the hair fibers were rinsed with running water for two minutes.

After rinsing, the hair fibers were immersed in 15 ml of the neutralizer and allowed to stand for three minutes. Then, the hair fibers were rinsed with running water for two minutes. Following the rinsing, the hair fibers were unwound from the aluminum mandrel and the obtained coil was immersed in water. Thereafter, both the length of the hair fiber and diameter of the resulting hair coil were recorded.

In permanently waving hair using this type of reducing agent, an acceptable curl has a curl diameter (D) ranging between about 7.00 and 10.40 mm, and a coil length (L) ranging between about 27 and 37 min. Using this data, the Deficiency in Wave Tightness (DIWT) is determined, which represents the overall waving efficiency of the reducing agent. In general, acceptable DIWT results range between about 8 and 60.00. The "Deficiency in Wave Tightness" or DIWT is calculated as follows:

$$DIWT = \frac{\text{diameter of hair coil (mm)} - \text{diameter of mandrel (mm)}}{\text{diameter of mandrel (mm)}} \times 100$$

In order to further demonstrate the advantages obtained by employing the reducing agents of the present invention, additional tests were conducted to determine the tensile strength of the hair fibers after permanent waving with the present invention and prior art reducing agents. As is well known, the 20% index is a measure of the hair fiber damage in the yield region and is defined as the force ratio of treated to untreated hair fiber at 20% elongation. This method is commonly used to evaluate the damage being imparted to hair fibers.

In order to effectively measure the tensile strength of the hair, an Instron Apparatus Model 1120 was used with each of the samples detailed herein. In each test, the resistant forces for each of the hair fibers was determined at 20% elongation under aqueous immersion conditions. The overall results attained from these elongation tests are provided below. The values provided represent the initial reading (prior to treatment) minus the final reading (after treatment) divided by the initial reading. As a result, the values closest to 1.000 indicate stronger relative tensile properties.

The final factor employed to objectively compare the test results detailed below is the Curl Value (CV). Curl Value is employed to effectively integrate the DIWT, the 20% index and the measured length of a resulting curl into a single number or value.

In determining the Curl Value in a particular test, the resulting permanently waved curl is measured and the DIWT, 20% index, and curl length are determined. Then, the results obtained for each factor are used to establish an overall Curl Value. The overall Curl Value is determined by employing the following Table of Values. Using the Table of Values, the results for each of the three factors are found in the Table, and the resulting Curl Value is established by integrating the impact of each of the three factors. Then, the integrated Curl Value is recorded.

| Curl Value Table | | | |
|---|---|---|---|
| CV | DIWT | Length (mm) | 20% Index |
| 1 | 0–9 | 20–25 | 0.9–1.00 |
| 2 | 10–19 | 25–30 | 0.8–0.89 |
| 3 | 20–29 | 30–35 | 0.7–0.79 |
| 4 | 30–39 | 35–40 | 0.6–0.69 |
| 5 | 40–49 | 40–45 | 0.5–0.59 |
| 6 | 50–59 | 45–50 | 0.4–0.49 |
| 7 | 60–69 | 50–55 | 0.3–0.39 |
| 8 | 70–79 | 55–60 | 0.2–0.29 |
| 9 | 80–89 | 60–65 | 0.1–0.19 |
| 10 | 90–100 | 65–70 | 0.0–0.09 |

As is evident from this Curl Value Table, a CV of 1 is the best that can be obtained when all three contributing factors are at their optimum level. In using the CV in comparing test results, a permanent wave lotion having a lower CV than other lotions indicates that the particular permanent wave lotion outperformed the other wave lotion in the combined results of their DIWT, measured length, and 20% index.

EXAMPLES

In order to demonstrate the efficacy and the improved permanent waving results attained by employing ethylcysteine in combination with a thiol compound selected from the group consisting of ammonium salts and glyceryl esters of thiopropionic acids, numerous tests were conducted at each different pH level using glyceryl monothiopropionate in combination with varying concentrations of ethylcysteine as the sole reducing agent. For comparative purposes, similar tests were also conducted using only glyceryl monothiopropionate as the sole reducing agent. In each formulation, ammonia was employed as the alkalizing agent.

By referring to Table II, the results obtained from this series of tests are detailed, with the diameter of the resulting curl (D), the length of the curl (L) and the DIWT being listed for each hair keratin reducing formulation tested at each of the different pH levels. In addition, for each test conducted and detailed in Table II, the resulting 20% index is also provided, along with the curl value.

TABLE II

Effect of Ethyl-Cysteine in Combination with GMTP

| | GMPT | | | | | GMTP + 0.5% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | | | | | | | | | | |
| 6.5 | | | | | | | | | | |
| 7.0 | 156.9 | 44.2 | 16.7 | .8186 | 22 | 113.9 | 33.0 | 13.9 | 80.73 | 16 |
| 7.5 | 96.2 | 35.2 | 12.8 | .7768 | 17 | 65.4 | 32.9 | 10.8 | .7425 | 14 |
| 8.0 | 44.6 | 34.9 | 9.4 | .7169 | 11 | 35.4 | 30.2 | 8.8 | .6730 | 11 |
| 8.25 | 27.7 | 28.7 | 8.3 | .6820 | 9 | 28.7 | 32.8 | 8.4 | .6004 | 10 |
| 8.50 | 17.5 | 28.4 | 7.6 | .6341 | 8 | 12.7 | 31.8 | 7.3 | .5545 | 10 |
| 8.75 | 11.2 | 30.3 | 7.2 | .5567 | 10 | 4.2 | 36.3 | 6.8 | .3934 | 12 |

| | GMPT + 1.0% E-Cysteine | | | | | GMTP + 2.0% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | 86.7 | 38.6 | 12.4 | .8072 | 15 | 107.7 | 43.1 | 13.5 | .8536 | 18 |
| 6.5 | 57.9 | 36.3 | 10.6 | .8024 | 12 | 70.8 | 39.7 | 10.9 | .8039 | 13 |
| 7.0 | 33.9 | 33.9 | 8.7 | .7517 | 10 | 50.3 | 37.9 | 9.5 | .7395 | 13 |
| 7.5 | 21.0 | 32.4 | 8.1 | .7136 | 9 | 25.1 | 38.0 | 7.9 | .6854 | 11 |
| 8.0 | 17.0 | 35.6 | 7.4 | .6461 | 10 | 6.7 | 36.2 | 7.1 | .6828 | 9 |
| 8.25 | | | | | | | | | | |
| 8.50 | | | | | | | | | | |
| 8.75 | | | | | | | | | | |

As is evident from the review of the test data detailed in Table II, the incorporation of ethyl-cysteine in combination with glyceryl monothiopropionate as the sole reducing agent for permanently waving hair provided substantially enhanced waving results at pH levels substantially lower than the pH levels required for use of glyceryl monothiopropionate independently. Furthermore, the hair resulting from the use of glyceryl monothiopropionate in combination with ethyl-cysteine provided hair fibers which were found to be softer to the feel.

Following substantially identical procedures employed in obtaining the results detailed in Table II, additional tests were also conducted to clearly demonstrate the efficacy and improved results attained by employing ethyl-cysteine in combination with a thiol compound selected from the group consisting of ammonium salts and glyceryl esters of thiolactic acid and thioglycolic acid. The results of these tests are detailed in Tables III, IV and V. In conducting the tests detailed in Table III, varying concentrations of ethyl-cysteine were employed in combination with glyceryl monothiolactate as the sole reducing agent at different pH levels. For comparative purposes, essentially identical tests were also conducted using only glyceryl monothiolactate as the sole reducing agent. In each formulation, ammonia was used as the alkalizing agent.

In the test data detailed in Table IV, glyceryl monothioglycolate was employed in combination with varying concentrations of ethyl-cysteine as the sole reducing agent at different pH levels. For comparative purposes, similar tests were conducted using only glyceryl monothioglycolate as the sole reducing agent with the results of these tests also detailed in Table IV. In each formulation, monoethanolamine was used as the alkalizing agent.

Finally, Table V contains the test results that were obtained by employing thiolactic acid in combination with varying concentrations of ethyl-cysteine as the sole reducing agent. For comparative purposes, similar tests were conducted using only thiolactic acid as the sole reducing agent. In each formulation, monoethanolamine was employed as the alkalizing agent.

By reviewing the test data contained in Tables III, IV, and V, the resulting curl (D) the length of the curl (L) and the DIWT for each hair keratin reducing formulation tested at each of the different pH levels is clearly shown. In addition, the resulting 20% index and the curl value was also provided for each test conducted.

TABLE III

Effect of Ethyl-Cysteine in Combination with GMTL

| | GMTL | | | | | GMTL + 0.5% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | | | | | | | | | | |
| 6.5 | | | | | | | | | | |
| 7.0 | 95.8 | 34.5 | 12.7 | .8040 | 15 | 58.5 | 31.0 | 10.3 | 80.33 | 11 |
| 7.5 | 30.8 | 31.1 | 8.5 | .7444 | 10 | 46.6 | 30.7 | 9.5 | .7674 | 11 |
| 8.0 | 60.0 | 33.5 | 10.4 | .8216 | 12 | 60.4 | 32.5 | 10.4 | .7919 | 13 |

TABLE III-continued

Effect of Ethyl-Cysteine in Combination with GMTL

| 8.25 | 106.1 | 37.4 | 13.4 | .8604 | 16 | 83.8 | 35.2 | 11.9 | .8347 | 15 |
| 8.50 | 123.1 | 40.9 | 14.5 | .8802 | 19 | 115.4 | 39.5 | 14.0 | .8658 | 17 |
| 8.75 | 163.1 | 45.9 | 17.1 | .8888 | 24 | 191.0 | 49.9 | 18.9 | .9086 | 26 |

| | GMTL + 1.0% E-Cysteine | | | | | GMTL + 2.0% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | 109.7 | 44.7 | 13.9 | .8453 | 17 | 107.7 | 38.0 | 13.5 | .8627 | 16 |
| 6.5 | 95.9 | 40.9 | 12.5 | .8198 | 17 | 69.7 | 32.2 | 10.7 | .8057 | 12 |
| 7.0 | 74.3 | 34.2 | 11.3 | .7895 | 14 | 38.5 | 31.7 | 9.0 | .7599 | 10 |
| 7.5 | 65.2 | 37.9 | 10.4 | .7737 | 14 | 30.0 | 30.9 | 8.5 | .7433 | 10 |
| 8.0 | 66.9 | 36.3 | 10.9 | .7659 | 14 | 41.9 | 31.3 | 9.2 | .7574 | 11 |
| 8.25 | | | | | | | | | | |
| 8.50 | | | | | | | | | | |
| 8.75 | | | | | | | | | | |

TABLE IV

Effect of Ethyl-Cysteine in Combination with GMTG

| | GMTG | | | | | GMTG + 0.5% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | | | | | | | | | | |
| 6.5 | | | | | | | | | | |
| 7.0 | 39.5 | 31.2 | 9.1 | .7203 | 10.0 | 33.5 | 30.1 | 8.68 | .7383 | 10 |
| 7.5 | 18.46 | 28.3 | 7.7 | .6466 | 8 | 30.4 | 30.6 | 8.48 | .7313 | 10 |
| 8.0 | 33.85 | 28.9 | 8.7 | .7871 | 9.0 | 41.9 | 30.4 | 9.23 | .7597 | 11 |
| 8.25 | 36.92 | 31.1 | 8.9 | .7860 | 10 | 42.7 | 30.8 | 9.28 | .7736 | 11 |
| 8.50 | 67.69 | 32.1 | 10.9 | .7955 | 13 | 63.7 | 34.5 | 10.6 | .8145 | 12 |
| 8.75 | 75.38 | 36.9 | 11.4 | .8367 | 14 | 107.7 | 40.0 | 13.5 | .8311 | 18 |

| | GMTG + 1.0% E-Cysteine | | | | | GMTG + 2.0% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 6.0 | 47.7 | 35.7 | 9.3 | .8073 | 11 | 36.9 | 30.7 | 8.9 | .7592 | 10 |
| 6.5 | 43.9 | 35.2 | 9.4 | .7862 | 12 | 26.2 | 28.3 | 8.2 | .7347 | 8 |
| 7.0 | 30.8 | 29.0 | 8.5 | .7867 | 9 | 14.4 | 30.2 | 7.3 | .7218 | 8 |
| 7.5 | 32.8 | 32.6 | 8.9 | .7612 | 10 | 7.2 | 30.4 | 6.9 | .7229 | 7 |
| 8.0 | 41.3 | 34.8 | 9.4 | .7598 | 11 | 14.4 | 29.7 | 7.3 | .7299 | 7 |
| 8.25 | | | | | | | | | | |
| 8.50 | | | | | | | | | | |
| 8.75 | | | | | | | | | | |

TABLE V

Effect of Ethyl-Cysteine in Combination with TLA

| | TLA | | | | | TLA + 0.5% E-Cysteine | | | | |
|---|---|---|---|---|---|---|---|---|---|---|
| pH | DIWT | L(mm) | D(mm) | 20% Index | CV | DIWT | L(mm) | D(mm) | 20% Index | CV |
| 8.0 | 68.7 | 40.9 | 10.9 | .7369 | 15 | 53.9 | 34.6 | 10.0 | .7298 | 12 |
| 8.50 | 33.1 | 36.6 | 8.7 | .7251 | 11 | 27.7 | 32.8 | 8.3 | .7081 | 9 |
| 8.75 | 26.2 | 33.8 | 8.2 | .6936 | 10 | 20.8 | 31.9 | 7.9 | .6126 | 10 |
| 9.00 | 20.4 | 33.2 | 7.8 | .5553 | 11 | 12.7 | 31.4 | 7.3 | .5041 | 10 |

TABLE V-continued

| | Effect of Ethyl-Cysteine in Combination with TLA | | | | | | | | | |
|---|---|---|---|---|---|---|---|---|---|---|
| | TLA + 1.0% E-Cysteine | | | | | TLA + 2.0% E-Cysteine | | | | |
| pH | DIWT | L(mm) | D(mm) | 20% Index | CV | DIWT | L(mm) | D(mm) | 20% Index | CV |
| 8.0 | 52.3 | 38.8 | 9.9 | .7707 | 13 | 42.1 | 39.5 | 9.4 | .6692 | 13 |
| 8.50 | 31.9 | 36.6 | 8.6 | .7455 | 11 | 33.9 | 33.8 | 8.7 | .6319 | 11 |
| 8.75 | 21.5 | 33.7 | 7.9 | .6827 | 10 | 19.0 | 33.5 | 7.6 | .5479 | 10 |
| 9.00 | 7.7 | 35.6 | 7.0 | .5945 | 10 | 18.5 | 31.2 | 7.7 | .4818 | 11 |

As is evident from a review of the test data provided in Tables III, IV and V, the incorporation of ethyl-cysteine in combination with glyceryl monothiolactate, glyceryl monothioglycolate, and thiolactic acid as the sole reducing agents for permanently waving hair provided substantially enhanced waving results at pH levels substantially lower than the pH levels required for effectively using glyceryl monothiolactate, glyceryl monothioglycolate, or thiolactate acid independently. Furthermore, in each of the tests wherein ethyl-cysteine was employed, in combination with either glyceryl monothiolactate, glyceryl monothioglycolate, or thiolactic acid, the permanently waved hair fibers were found to be softer to the feel and more manageable than the hair fibers resulting from permanent waving with only glyceryl monothiolactate, glyceryl monothioglycolate, or thiolactic acid.

In order to further demonstrate the efficacy of employing other lower alkyl esters of cysteine, additional tests were conducting employing methyl cysteine in combination with thiol compounds selected from the group consisting of glyceryl esters of thiopropionic acid and thiolactic acid. The results of these tests are detailed in Tables VI and VII. In conducting the tests detailed in Tables VI and VII, substantially identical procedures were employed as detailed above in reference to Tables II–V.

In conducting the tests detailed in Table VI, a concentration of 2% methyl cysteine was employed in combination with glyceryl monothiopropionic as the sole reducing agent at different pH levels. In order to adjust the pH level, ammonia was used as the alkalizing agent. The results attained are detailed in Table VI along with, for comparative purposes, the results obtained when glyceryl monothiopropionate was employed independently as well as employed in combination with 2% ethyl cysteine.

Table VII presents the test results obtained from employing a 2% concentration of methyl cysteine in combination with glyceryl monothiolactate as the sole reducing agent at different pH levels. In these tests, ammonia was used as the alkalizing agent. Also included in Table VII, for comparative purposes, are the results obtained using only glyceryl monothiolactate as the sole reducing agent and glyceryl monothiolactate in combination with 2% ethyl cysteine.

TABLE VI

| | Effect of Methyl-Cysteine in Combination with GMTP | | | | | | | | | | | | | | |
|---|---|---|---|---|---|---|---|---|---|---|---|---|---|---|---|
| | GMTP | | | | | GMTP + 2.0 E-Cysteine | | | | | GMTP + 2.0% M-Cysteine | | | | |
| pH | DIWT | L(mm) | D(mm) | 20% Index | CV | DIWT | L(mm) | D(mm) | 20% Index | CV | DIWT | L(mm) | D(mm) | 20% Index | CV |
| 6.0 | | | | | | 107.7 | 43.1 | 13.5 | .8536 | 18 | 112.7 | 43.3 | 13.8 | .8388 | 19 |
| 6.5 | | | | | | 70.8 | 39.7 | 10.9 | .8039 | 13 | 66.2 | 37.4 | 10.8 | .7994 | 14 |
| 7.0 | 156.9 | 44.2 | 16.7 | .8186 | 22 | 50.3 | 37.9 | 9.5 | .7395 | 13 | 45.1 | 35.8 | 9.4 | .7251 | 12 |
| 7.5 | 96.2 | 35.2 | 12.8 | .7768 | 17 | 25.1 | 38.0 | 7.9 | .6854 | 11 | 27.7 | 36.2 | 8.3 | .6850 | 11 |
| 8.0 | 44.2 | 34.9 | 9.4 | .7169 | 11 | 6.7 | 36.2 | 7.1 | .6828 | 9 | 17.5 | 36.2 | 7.6 | .6002 | 10 |
| 8.25 | 27.7 | 28.7 | 8.3 | .6820 | 9 | | | | | | | | | | |
| 8.50 | 17.5 | 28.4 | 7.6 | .6341 | 8 | | | | | | | | | | |
| 8.75 | 11.2 | 30.3 | 7.2 | .5567 | 10 | | | | | | | | | | |

TABLE VII

| | Effectr of Methyl-Cysteine in Combination with GMTL | | | | | | | | | | | | | | |
|---|---|---|---|---|---|---|---|---|---|---|---|---|---|---|---|
| | GMTL | | | | | GMTL + 2.0 E-Cysteine | | | | | GMTL + 2.0% M-Cysteine | | | | |
| pH | DIWT | L(mm) | D(mm) | 20% Index | CV | DIWT | L(mm) | D(mm) | 20% Index | CV | DIWT | L(mm) | D(mm) | 20% Index | CV |
| 6.0 | | | | | | 107.7 | 38.0 | 13.5 | .8627 | 16 | 90.4 | 36.2 | 12.4 | .8439 | 16 |
| 6.5 | | | | | | 69.7 | 32.2 | 10.7 | .8057 | 12 | 55.4 | 34.9 | 10.1 | .7944 | 12 |
| 7.0 | 95.8 | 34.5 | 12.7 | .8040 | 15 | 38.7 | 31.7 | 9.0 | .7599 | 10 | 29.3 | 31.6 | 8.4 | .7664 | 9 |
| 7.5 | 30.8 | 31.1 | 8.5 | .7444 | 10 | 30.0 | 30.9 | 8.5 | .7433 | 10 | 38.1 | 33.2 | 9.0 | .7234 | 10 |

TABLE VII-continued

Effectr of Methyl-Cysteine in Combination with GMTL

| | GMTL | | | | | GMTL + 2.0 E-Cysteine | | | | | GMTL + 2.0% M-Cysteine | | | | |
|---|---|---|---|---|---|---|---|---|---|---|---|---|---|---|---|
| pH | DIWT | L(mm) | D(mm) | 20% Index | CV | DIWT | L(mm) | D(mm) | 20% Index | CV | DIWT | L(mm) | D(mm) | 20% Index | CV |
| 8.0 | 60.0 | 33.50 | 10.4 | .8216 | 12 | 41.9 | 31.3 | 9.2 | .7574 | 11 | 49.3 | 36.5 | 9.7 | .7412 | 12 |
| 8.25 | 106.1 | 37.40 | 13.4 | .8604 | 16 | | | | | | | | | | |
| 8.50 | 123.1 | 40.90 | 14.5 | .8802 | 19 | | | | | | | | | | |
| 8.75 | 163.1 | 45.90 | 17.1 | .8888 | 24 | | | | | | | | | | |

As is evident from a review of the results detailed in Tables VI and VII, the use of methyl cysteine in combination with a thiol compound as the sole reducing agent provides substantially superior results over the thiol compound alone. Furthermore, the substantially enhanced permanent wave results are attained at pH levels substantially lower than the pH level required for effectively permanently waving the hair when the thiol compound is used independently.

In addition, it is also evident that methyl cysteine in combination with the thiol compound produces results substantially equivalent to the results attained by the use of ethyl cysteine with the same thiol compound. In addition to the performance results detailed in Tables VI and VII, the permanently waved hair fibers resulting from the use of methyl cysteine were also found to be softer to the feel and more manageable than hair fibers resulting from permanently waving with only the thiol compound. As a result, ethyl-cysteine, methyl-cysteine, and other comparable lower alkyl esters of cysteine can be employed with equal efficacy.

It will thus be seen that the objects set forth above, among those made apparent from the preceding description, are efficiently attained and, since certain changes may be made in carrying out the above process, and in the compositions set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood in the claims, ingredients or compounds recited in the singular are intended to include compatible mixtures of such ingredients wherever the sense permits.

Having described our invention, what we claim as new and desire to secure by Letters Patent is:

1. A hair reducing or permanent waving lotion for use in the permanent waving of hair, said lotion comprising
   A. a reducing agent consisting essentially of
      a. between about 0.01% and 5% by weight of the total composition of a lower alkyl ester of cysteine wherein said alkyl radical has a carbon chain length ranging between one and three, and
      b. between about 5% and 25% of the total composition of one thiol compound selected from the group consisting of glycerol monothiopropionate, glycerol monothiolactate, and glycerol monothioglycolate; and
   B. one or more agents selected from the group consisting of surfactants, alkalizing agents, fragrances, conditioning agents and water.

2. The permanent waving lotion defined in claim 1, wherein the lower alkyl ester of cysteine is further defined as comprising one selected from the group consisting of methyl-ester cysteine, ethyl-ester cysteine, and propyl-ester cysteine.

3. The permanent waving lotion defined in claim 2, wherein said alkalizing agent is further defined as comprising one selected from the group consisting of ammonia, ammonium hydroxide, monoethanolamine, guanidine, diethanolamine, triethanolamine, ammonium carbonate, and bicarbonate in sufficient amount to adjust the pH of the lotion to range between about 5.0 and 9.5.

4. The permanent waving lotion defined in claim 1, wherein said agents are further defined as comprising
   a. between about 0.1% and 4% by weight of the total composition of the surfactant,
   b. between about 0.1% and 6% by weight of the total composition of the conditioning agents,
   c. between about 0.1% and 10% by weight of the total composition of the alkalizing agent,
   d. between about 0.5% and 3% by weight of the total composition of the fragrance, and
   e. water forming the balance of the total composition.

5. A process for providing enhanced permanent waving of hair at a reduced pH level, said process comprising the steps of
   A. forming a permanent waving lotion comprising
      a. a reducing agent consisting essentially of
         1. between about 0.01% and 5% by weight of the total composition of a lower alkyl ester of cysteine wherein said alkyl radical has a carbon chain length ranging between one and three, and
         2. between about 5% and 25% of the total composition of one thiol compound selected from the group consisting of glycerol monothiopropionate, glycerol monothiolactate, and glycerol monothioglycolate; and
      b. between about 0.1% and 4% by weight of the total composition of a surfactant,
      c. between about 0.1% and 6% by weight of the total composition of a conditioning agent,
      d. between about 0.1% and 10% by weight of the total composition of an alkalizing agent,
      e. between about 0.5% and 3% by weight of the total composition of a fragrance, and
      f. water forming the balance;
   B. moistening hair to be permanently waved;
   C. rolling the moistened hair fibers onto curlers for securement thereto;
   D. applying the permanent waving lotion to the rolled hair fibers;
   E. allowing the permanent waving lotion to remain on the hair for between about 10 and 60 minutes;

F. rinsing the hair with water and blotting to remove excess moisture; and

G. neutralizing or oxidizing the hair by employing a solution comprising one or more agents selected from the group consisting of acidic hydrogen peroxide, bromate, and sodium chlorite.

6. The process defined in claim 5, wherein the lower alkyl ester of cysteine is further defined as comprising one selected from the group consisting of methyl-ester cysteine, ethyl-ester cysteine, and propyl-ester cysteine.

7. The process defined in claim 6, wherein the neutralizing or oxidizing solution is further defined as comprising a bromate salt selected from the group consisting of sodium, potassium, and ammonium with a pH ranging between about 3 and 9.

8. The process defined in claim 5, wherein the neutralizing or oxidizing solution comprises sodium chlorite with a pH ranging between about 3 and 10.

9. The process defined in claim 5, wherein the neutralizing or oxidizing solution further comprises a water soluble salt selected from the group consisting of sulfites and bisulfites to provide an exothermic reaction.

10. The process defined in claim 5, wherein said permanent waving lotion is further defined as comprising an alkalizing agent selected from the group consisting of ammonia, ammonium hydroxide, monoethanolamine, guanidine, diethanolamine, triethanolamine, ammonium carbonate, and bicarbonate in sufficient amount to adjust the pH of the permanent waving lotion to range between about 5.0 and 9.5.

11. The process defined in claim 10, comprising the additional step of

H. heating the hair during the processing of the permanent waving lotion.

12. The process defined in claim 11, wherein said hair is further defined as being heated to a temperature of about 50° C.

13. The process defined in claim 10, wherein the permanent waving lotion is further defined as being prepared by intermixing all of the components therefor except the reducing agent components and intermixing the reducing agent components with the previously prepared components immediately prior to applying the permanent waving lotion to the head of hair to be permanently waved.

14. The process defined in claim 13, wherein the permanent waving lotion is further defined as being prepared by separately intermixing the reducing agent components with the alkalizing agent, with said alkalizing agent having a quantity sufficient to enable the pH level of the permanent waving lotion to range between about 5.0 and 9.5.

15. A hair reducing or permanent waving lotion for use in the permanent waving of hair, said lotion comprising A. a reducing agent consisting essentially of
  a. between about 0.01% and 5% by weight of the total composition of a lower alkyl ester of cysteine wherein said alkyl radical has a carbon chain length ranging between one and three, and
  b. between about 5% and 25% of the total composition of one thiol compound selected from the group consisting of glycerol monothiopropionate, glycerol monothiolactate, and glycerol monothioglycolate;
  c. between about 0.1% and 4% by weight of the total composition of a surfactant,
  d. between about 0.1% and 6% by weight of the total composition of a conditioning agent,
  e. between about 0.1% and 10% by weight of the total composition of an alkalizing agent,
  f. between about 0.5% and 3% by weight of the total composition of a fragrance, and
  g. water forming the balance.

* * * * *